United States Patent
Kim et al.

(12) 
(10) Patent No.: US 7,734,425 B2
(45) Date of Patent: Jun. 8, 2010

(54) APPARATUS AND METHOD FOR SEARCHING PROTEIN ACTIVE SITE

(75) Inventors: Dae Hee Kim, Daejeon (KR); Sung Hee Park, Daejeon (KR); Chan Yong Park, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 389 days.

(21) Appl. No.: 11/505,397

(22) Filed: Aug. 17, 2006

(65) Prior Publication Data

US 2007/0136000 A1    Jun. 14, 2007

(30) Foreign Application Priority Data

Dec. 8, 2005    (KR) ...................... 10-2005-0120191
Feb. 13, 2006    (KR) ...................... 10-2006-0013695

(51) Int. Cl.
*G06F 19/00*    (2006.01)
*G01N 31/00*    (2006.01)
*G06G 7/58*    (2006.01)

(52) U.S. Cl. .............................. 702/19; 702/27; 703/11

(58) Field of Classification Search ........................ None
See application file for complete search history.

(56) References Cited

U.S. PATENT DOCUMENTS

2003/0096307 A1*    5/2003    Fetrow ........................ 435/7.1

FOREIGN PATENT DOCUMENTS

KR    1020050046960    5/2005
KR    1020050064644    6/2005

OTHER PUBLICATIONS

Holm et al. (Proceedings of International Conference on Intelligent Systems for Molecular Biology; ISMB. International Conference on Intelligent Systems for Molecular Biology 1995;3():179-87).*
Liisa Holm et al.; "Protein Structure Comparison by Alignment of Distance Matrices"; J.Mol. Biol. (1993) 233; pp. 123-138.
Shann-Ching Chen et al.; "Protein Retrieval by Matching 3D Surfaces"; pp. 1-4, 2002.

* cited by examiner

*Primary Examiner*—Lori A Clow
(74) *Attorney, Agent, or Firm*—Lowe Hauptman Ham & Berner LLP

(57) ABSTRACT

Provided are an apparatus and method of searching a protein active site. The apparatus includes a database which stores information on a plurality of reference active sites, a comparing unit which calculates 3D structural similarities according to the number of overlapping residues, with respect to an input active site and the stored reference active site, and a search unit which searches the reference active site with respect to the input active site according to the similarities. Accordingly, similar active sites can be searched with a low computational complexity, thereby be used for a correct new drug design.

10 Claims, 9 Drawing Sheets

FIG. 3

| PROTEIN NAME | LIST OF PROTEIN ACTIVE SITE | LOCATION DATA OF N, C$_\alpha$, AND C ATOMS OF RESIDUES CONSTITUTING ACTIVE SITE | LIST OF RESIDUES CONSTITUTING ACTIVE SITE | ORTHONORMAL VECTOR FOR EACH RESIDUE |
|---|---|---|---|---|
| ace | ace_pocket_1 | ILE N −9.443 51.614 71.638<br>ILE CA −9.676 52.463 72.792<br>ILE C −10.261 51.717 73.998<br>LEU N −10.261 52.238 75.121<br>LEU CA −10.551 53.667 72.323<br>LEU C −9.670 54.907 72.207<br>. . . | ILE<br>LEU<br>. . . | $\begin{bmatrix} 1 & 2 & 3 \\ 4 & 5 & 6 \\ 7 & 8 & 9 \end{bmatrix}$ $\begin{bmatrix} 0 & 2 & 3 \\ 4 & 2 & 6 \\ 3 & 8 & 7 \end{bmatrix}$ |
| | ace_pocket_2 | | | |
| | ace_pocket_3 | | | |
| | ace_pocket_4 | | | |

APPARATUS AND METHOD FOR SEARCHING PROTEIN ACTIVE SITE

CROSS-REFERENCE TO RELATED PATENT APPLICATION

This application claims the benefit of Korean Patent Application Nos. 10-2005-0120191, filed on Dec. 8, 2005 and 10-2006-0013695, filed on Feb. 13, 2006 in the Korean Intellectual Property Office, the disclosures of which are incorporated herein in their entirety by reference.

BACKGROUND NODE OF THE INVENTION

1. Field of the Invention

The present invention relates to an apparatus and method of searching a protein active site, and more particularly, to an apparatus and method of searching a protein active site, which detect and provide a similarity between a protein active site playing a crucial role in new drug development and other active sites by approaching a feature of the protein active site in a 3D manner.

2. Description of the Related Art

In past related researches, methods of searching similar shaped-proteins have been proposed, but protein active sites have not been subject to a comparison search. Conventionally, various methods of comparing protein structures include a method of comparing a distance between protein atoms, and a method of measuring a similarity of protein atoms by using only the location of a protein alpha-carbon. In addition, a method using geometric hashing has also been proposed. However, computational complexity increases in proportion to a square of the protein size, and therefore more calculation time is required.

SUMMARY OF THE INVENTION

The present invention provides an apparatus and method of searching a protein active site, in which similar active sites can be correctly searched with a low computational complexity.

According to an aspect of the present invention, there is provided an apparatus for searching a protein active site, the apparatus comprising: a database which stores information on a plurality of reference active sites; a comparing unit which calculates 3D structural similarities according to the number of overlapping residues of an input active site and the stored reference active site; and a search unit which searches the reference active site while referring to the input active site according to the similarities.

According to another aspect of the present invention, there is provided a method of searching a protein active site, the method comprising: storing information on a plurality of reference active sites; calculating 3D structural similarities according to the number of overlapping residues of an input active site and the stored reference active site; and searching the reference active site while referring to the input active site according to the similarities.

BRIEF DESCRIPTION OF THE DRAWINGS

The above and other features and advantages of the present invention will become more apparent by describing in detail exemplary embodiments thereof with reference to the attached drawings in which:

FIG. 3 illustrates a DB table for searching an active site according to an embodiment of the present invention;

DETAILED DESCRIPTION OF THE INVENTION

Hereinafter, the present invention will be described in detail by explaining exemplary embodiments of the invention with reference to the attached drawings.

In a new drug development using structural genomics, a drug is designed so that protein active sites can be structurally bonded by 3D modeling a protein shape. In practice, when a newly designed drug, for example, Viagra, is bonded with not only an active site of a protein to be processed but also a similar active site of another protein not to be processed, it may cause various side-effects such as headache, flushing, indigestion, heart attack, etc. Therefore, such similar active sites need to be correctly searched with a low computational complexity, which may lead to a more precise new drug design. Since the 3D structure of a protein active site is pocket-shaped (concave), in a method according to an embodiment of the present invention, an active site, that is, a pocket, is extracted from a protein, data of the active site is stored in a database (DB), and a desired active site is compared with other active sites stored in the DB, thereby finding a similar active site. That is, in an embodiment of the present invention, an active site is represented as a reference frame of a residue in a 3D structure space, and is searched by using a geometric hashing method. A convex hull is configured by using Delaunay triangulation, which is generally used to extract an active site, a protein surface is constructed by using an alpha shape method, the active site is reconfigured by using a discrete flow method, and an active site search is carried out with respect to a residue based on the geometric hashing method.

Figure 1:
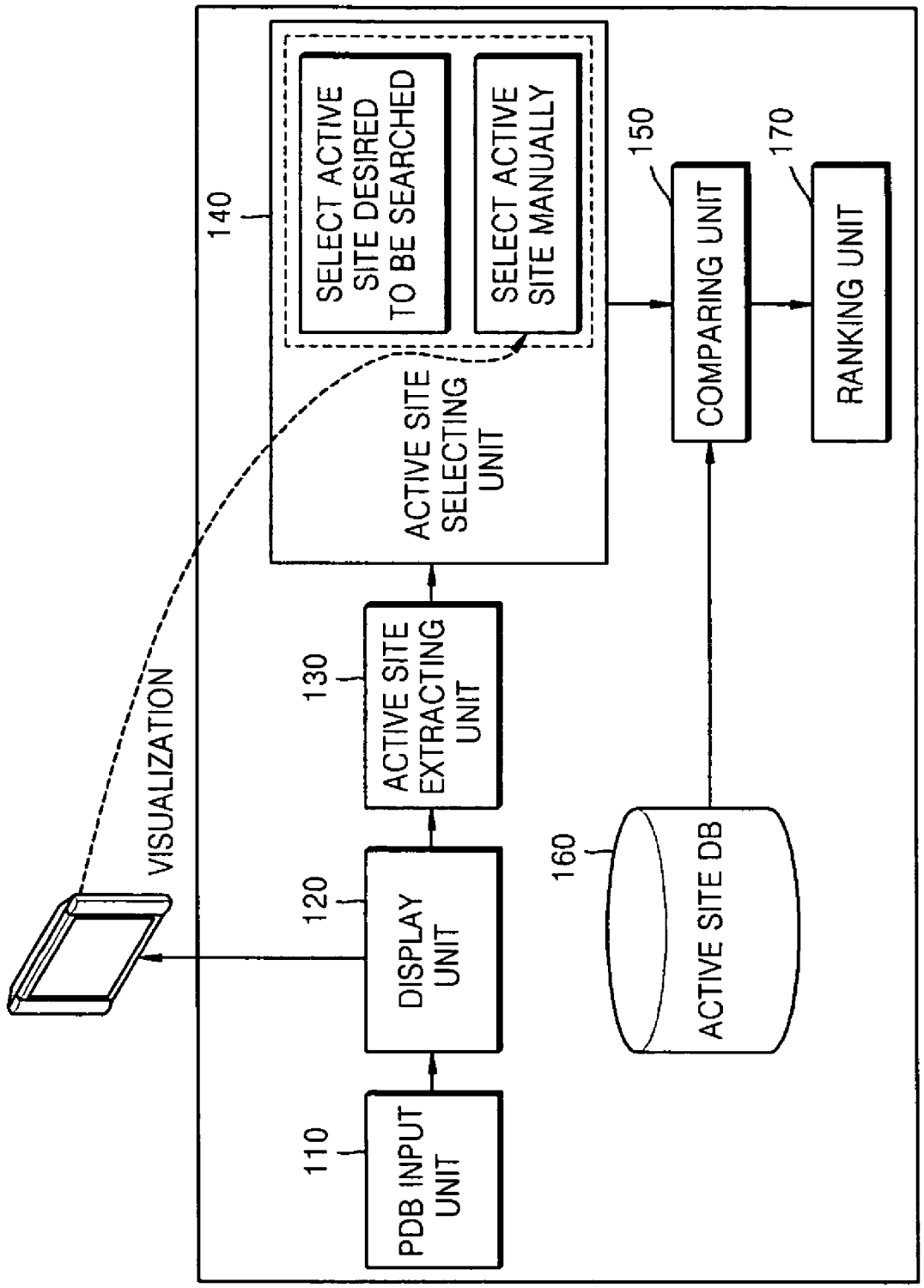
FIG. 1 is a block diagram of an apparatus for searching a protein active site according to an embodiment of the present invention.

FIG. 1 is a block diagram of an apparatus for searching a protein active site according to an embodiment of the present invention. The apparatus includes a protein data bank (PDB) input unit 110, a display unit 120, an active site extracting unit 130, an active site selecting unit 140, a comparing unit 150, an active site DB 160, and a ranking unit 170.

The PDB input unit 110 receives an input of a protein in the form of a PDB.

The display unit 120 visualizes a 3D structure of a protein from an input PDB file. In other words, the input PDB file is displayed on a screen based on atomic coordinates, and thus an atom and a residue included in an active site to be searched can be selected.

The active site extracting unit 130 extracts the active site from the input PDB file.

The active site selecting unit 140 selects an active site to be subject to a comparison-search with a reference active site stored in the DB 160 from protein active sites stored in the input PDB file, and provides the active site to the comparing unit 150. The selecting can be performed by a user who may select one of the active sites extracted by the active site extracting unit 130. Alternatively, the user may select an atom or a residue displayed on the display unit 120, and then an active site including the selected atom or residue may be selected to be provided to the comparing unit 150. However, the present invention is not limited thereto. In the former case, the user selects an active site to be subject to a comparison-search from active sites that are automatically extracted. In the latter case, a desired active site displayed on a screen is manually selected at an atomic level, and is then input to the comparing unit 150.

The comparing unit 150 searches an active site similar to the active site (that is, the input active site) selected by the active site selecting unit 140 from the active site DB 160 by using 3D geometric hashing. The comparing unit 150 calculates 3D structural similarity with respect to the input active site and the stored reference active site. For convenience, in this description, the selected active site will be referred to as an input active site, and the active site stored in the active site DB 160 (that is, the active site to be compared with the input active site) will be referred to as a reference active site.

The active site DB 160 stores information on the reference active site in the form of a DB by pre-processing. That is, information on a plurality of reference active sites is stored. An example of a DB format is shown in FIG. 3, which will be described below.

If the apparatus of FIG. 1 is a search unit which searches the reference active site with respect to the input active site according to the calculated similarity, the ranking unit 170 can rank a plurality of similarities calculated by the comparing unit 150 and provides information on the reference active site having a higher priority. That is, the ranking unit 170 displays a search result according to ranks of similarities.

Figure 2A:
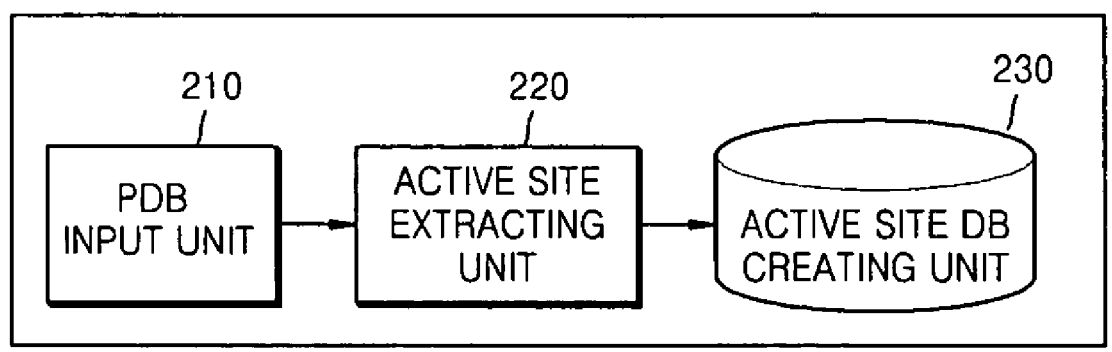
FIG. 2A is a block diagram of an active site database (DB) of FIG. 1 according to an embodiment of the present invention.

FIG. 2A is a block diagram of the active site DB 160 according to an embodiment of the present invention. The active site DB 160 includes a PDB input unit 210, an active site extracting unit 220, and an active site DB creating unit 230.

Figure 2B:
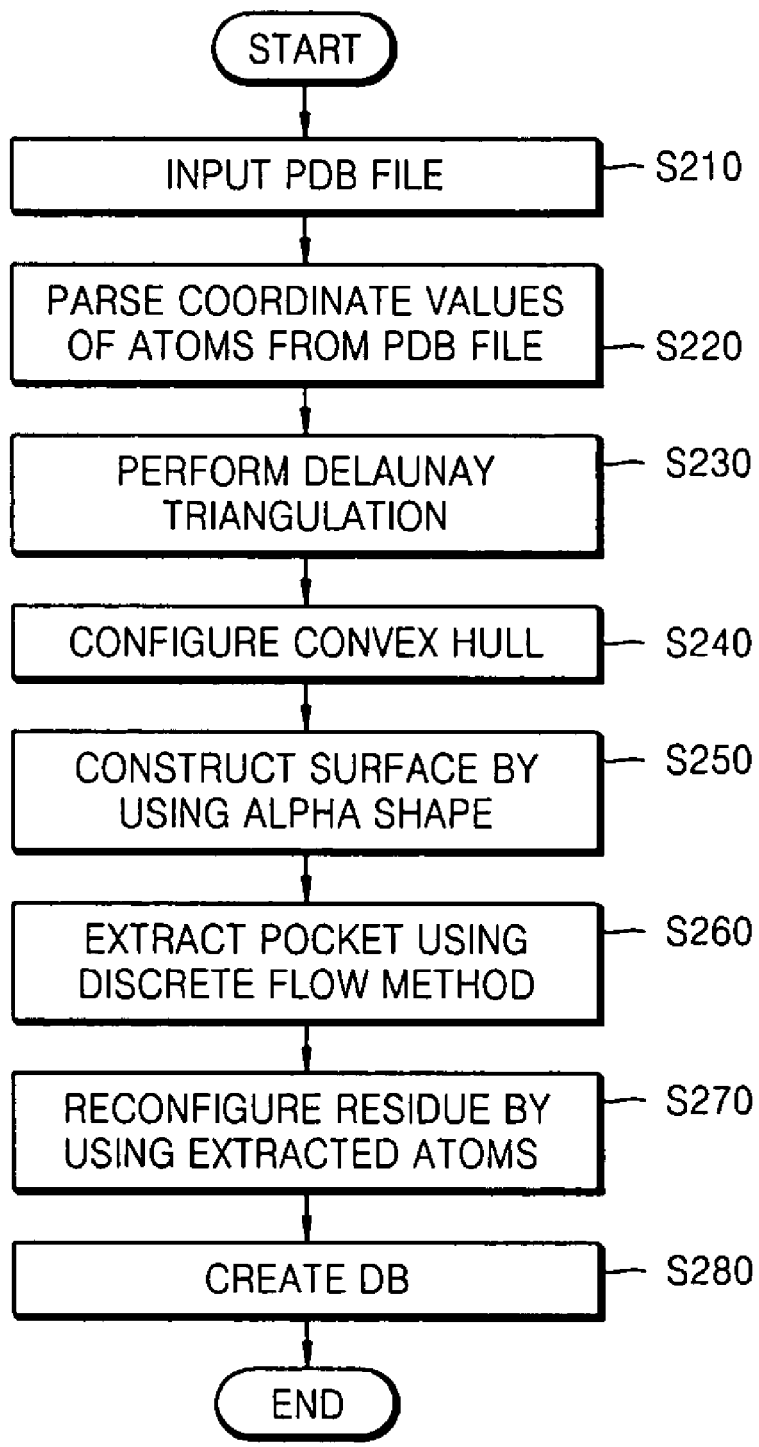
FIG. 2B is a flowchart illustrating a method of creating an active site DB according to an embodiment of the present invention.

FIG. 2B is a flowchart illustrating a method of creating an active site DB according to an embodiment of the present invention.

The process of creating the active site DB will now be descried with reference to FIGS. 2A and 2B.

The PDB input unit 210 receives an input of a PDB including information on a protein to be processed (operation S210).

The active site extracting unit 220 extracts an active site from an input PDB file. The following is an example of a detailed extracting process. Based on the PDB file, coordinate values of protein atoms are parsed (operation S220), Delaunay triangulation is then performed using the coordinate values (operation S230), and a convex hull is then configured (operations S240). Thereafter, a protein surface is configured according to an alpha shape method using an appropriate alpha value with respect to the configured convex hull (operation S250), and an active site is then extracted using a discrete flow method (operation S260).

The active site DB creating unit 230 creates information on the extracted active site in a specific DB format. An example of a table for the specific DB format can be seen in FIG. 3. The following is an example of creating a DB. Each active site is composed of atomic coordinates, and residues including each atom are reconfigured as an active site (operation S270). Here, the active site is composed of at least one residue. Through a series of processes described above, the DB format of FIG. 3 is created and then is stored in a process which will be described later (operation S280). If there is another protein of which structure is known and an active site is desired to be extracted, a DB is configured by using a PDB file in the same manner as above.

Unlike FIG. 2A, the active site DB 160 may be configured by storing only the content of FIG. 3, which will be described later. Here, the PDB input unit 210, the active site extracting unit 220, and the active site DB creating unit 230 operate in advance by performing pre-processing to create the active site DB 160.

FIG. 3 illustrates a DB table for searching an active site according to an embodiment of the present invention. The DB format illustrated in FIG. 3 is used when the active site DB 160 of FIG. 1 stores information on the active site.

Referring to FIG. 3, the DB table includes a total of five records which are a protein name, a list of protein active sites, location data of N, Cα (alpha carbon), and C atoms of residues constituting an active site, a list of residues constituting an active site, and an orthonormal vector for each residue. The protein name is stored in the first record. In the second record, according to the number of residues constituting an active site extracted from each protein, each active site is listed along with its affix, where an active site having the largest number of residues is numbered 1. Coordinate data of N, Cα, and C atoms of residues constituting an active site is stored in the third record, whereas coordinate data of other atoms are omitted. For example, when an active site includes ten residues, ten sets of coordinates data of N, Cα, and C atoms are stored. A list of residues constituting an active site is written in the fourth record. An orthonormal vector for each residue is calculated and written in the fifth record.

Figure 4:
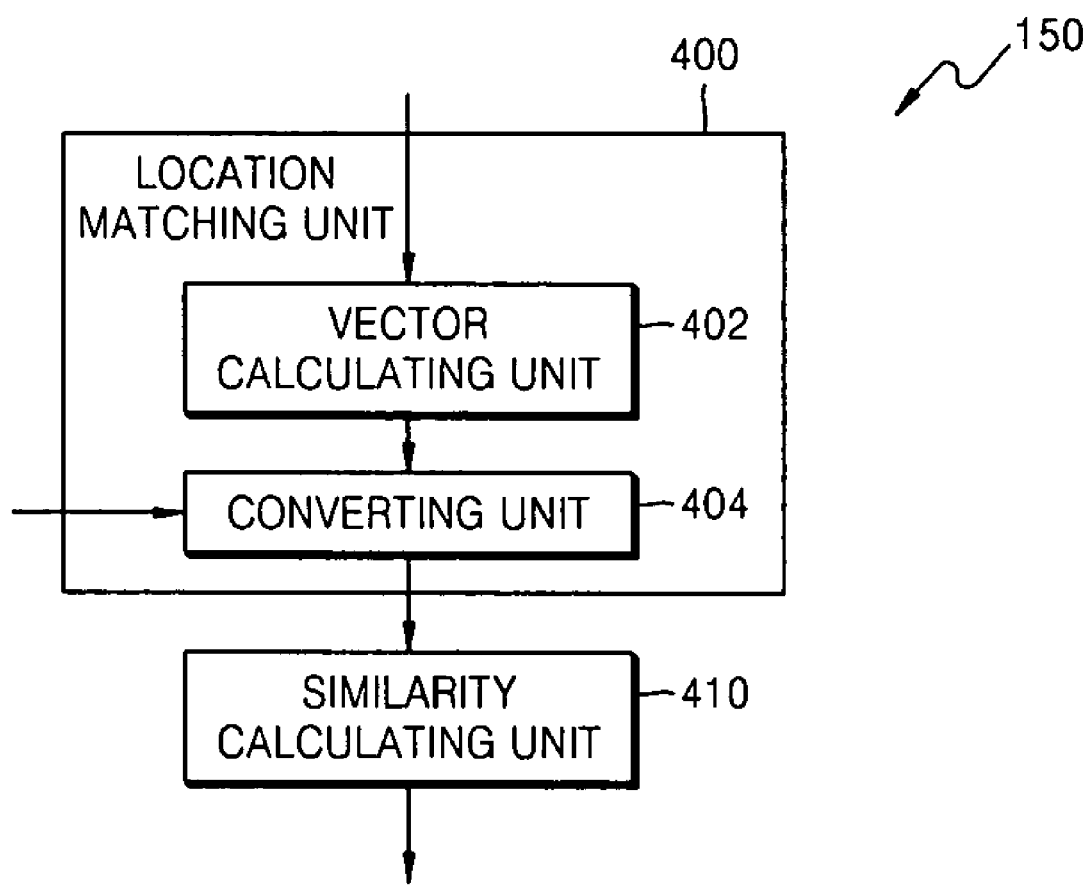
FIG. 4 is a block diagram of a comparing unit of FIG. 1.

FIG. 4 is a block diagram of the comparing unit 150 of FIG. 1. The comparing unit 150 includes a location matching unit 400 and a similarity calculating unit 410.

The location matching unit 400 matches the location of the input active site with the location of the reference active site, so that at least one of the residues included in the input active site and overlaps one of the residues included in the reference active site.

The similarity calculating unit 410 calculates the aforementioned similarity based on the number of residues overlapping between the input active site and the reference active site when the location matching is performed.

Figure 5A:
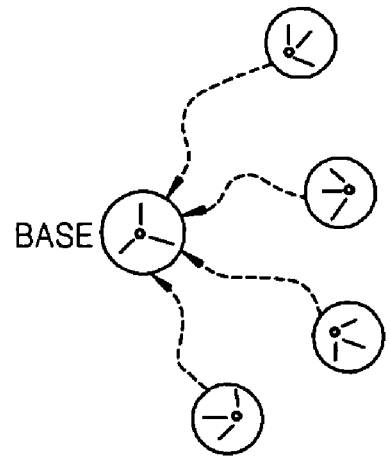
FIGS. 5A and 5B respectively illustrate examples of an input active site and a reference active site, to describe the comparing unit 150.
Figure 5B:
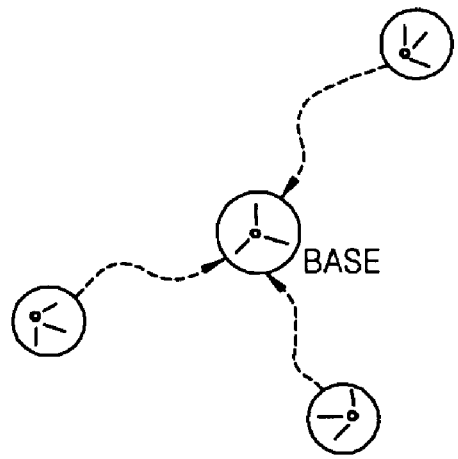

FIGS. 5A and 5B respectively illustrate examples of an input active site and a reference active site. The comparing unit 150 will be described with reference to FIGS. 5A and 5B.

When a residue indicated by BASE in FIG. 5A is matched with a residue indicated by BASE in FIG. 5B, two more residues overlap in addition to the two residues indicated by BASE, and in this case, the number of similarities is three. In principle, location matching and similarity calculating based on the location matching are performed for all residues. Since five residues are included in the active site of FIG. 5A, and four residues are included in the active site of FIG. 5B, the operations (location matching and similarity calculating) are performed twenty times. However, if a similarity calculated by a method (to be described later) is greater than a critical value, the location matching and the similarity calculating may be skipped for the rest of the residues not processed, and a next active site may be searched.

An embodiment of the present invention uses a feature that each residue of a protein includes N, Cα, and C atoms, and a distance between each of the N, Cα, and C atoms is constant. The matching operation of the present embodiment will now be described in detail with reference to FIG. 6.

Figure 6:
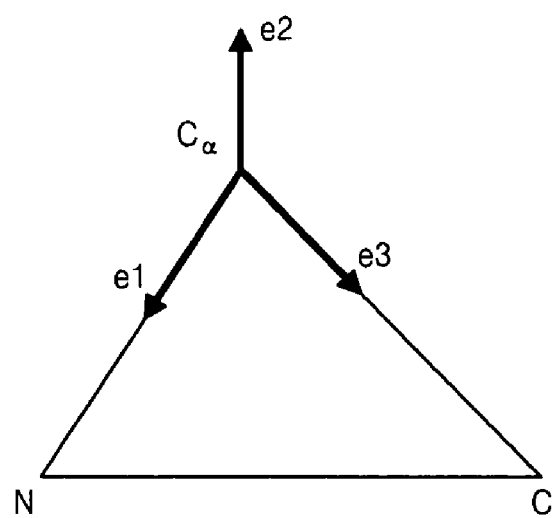
FIG. 6 illustrates a 3D reference frame used in an active site search according to an embodiment of the present invention.

FIG. 6 illustrates a 3D reference frame used in an active site search according to an embodiment of the present invention. Here, the N, Cα, and C atoms included in each residue are used.

In the present embodiment, in order to set a reference frame of a residue, orthonormal vectors $\vec{e_1}$, $\vec{e_2}$, $\vec{e_3}$ are obtained with the origin at Cα, and a rotation-transform and a shift-transform are carried out. Here, the orthonormal vectors $\vec{e_1}$, $\vec{e_2}$, $\vec{e_3}$ are obtained according to the following Formula 1.

$$\vec{e_1} = \frac{\overrightarrow{C_aN}}{\|\overrightarrow{C_aN}\|}$$

$$\vec{e_2} = \frac{\vec{e_1} \times \overrightarrow{C_aC}}{\|\vec{e_1} \times \overrightarrow{C_aC}\|}$$

$$\vec{e_3} = \vec{e_2} \times \vec{e_1}$$

[Formula 1]

By using the feature that each residue of a protein includes N, Cα, and C atoms, and a distance between each of the N, Cα, and C atoms is constant, as shown in FIG. 3, the active site DB 160 stores a name of a protein, a name of an active site included in the protein, a name of a residue included in the active site, coordinate data of N, Cα, and C atoms of the residue, and an orthonormal vector of the residue. The location matching unit 400 includes a vector calculating unit 402 and a converting unit 404.

The vector calculating unit 402 calculates orthonormal vectors of each residue based on the coordinate data of N, Cα, and C atoms of the residue included in the input active site. In the case of FIG. 5A, since five residues are included in the active site, five sets of orthonormal vectors are calculated using Formula 1.

By using a set of orthonormal vectors calculated by the vector calculating unit 402 and a set of orthonormal vectors stored in the active site DB 160, the converting unit 404 performs the rotation-transform and the shift-transform with respect to the coordinates included in the input active site and the coordinates included in the reference active site. If the active site of FIG. 5B is currently being processed as the reference active site stored in the active site DB 160, four sets of orthonormal vectors stored therein are used in the converting unit 404 to transform the active site.

The rotation-transform is performed using Formula 2. This is a process in which coordinates of all residues included in the active site are rotation-transformed into the orthonormal vectors ($\vec{e_1}$, $\vec{e_2}$, $\vec{e_3}$) of each residue, thereby creating new coordinates. Here, the orthonormal vectors ($\vec{e_1}$, $\vec{e_2}$, $\vec{e_3}$) are respectively represented as $(e_{1_x}, e_{1_y}, e_{1_z})$, $(e_{2_x}, e_{2_y}, e_{2_z})$, and $(e_{3_x}, e_{3_y}, e_{3_z})$. Coordinate data of a residue to be transformed among residues of an input active site is represented as $\vec{N} = (N_x, N_y, N_z)$, $\vec{C_a} = (C_{a_x}, C_{a_y}, C_{a_z})$ and $\vec{C} = (C_x, C_y, C_z)$. Transformed coordinate data is represented as $\vec{N'}$, $\vec{C_a'}$, $\vec{C'}$.

$$\left| \begin{bmatrix} \vec{N'} \\ \vec{C_a'} \\ \vec{C'} \end{bmatrix} \right| = \begin{bmatrix} N_x & N_y & N_z \\ C_{a_x} & C_{a_y} & C_{a_z} \\ C_x & C_y & C_z \end{bmatrix} \times \begin{bmatrix} e_{1_x} & e_{2_x} & e_{3_x} \\ e_{1_y} & e_{2_y} & e_{3_y} \\ e_{1_z} & e_{2_z} & e_{3_z} \end{bmatrix}$$

[Formula 2]

In the input active site of FIG. 5A, five residues are present, and coordinate data of the five residues is included in a coordinate set. If the coordinate set is rotation-transformed by using each set of orthonormal vectors, five more coordinate sets are created. Referring to Formula 2, one residue ($\vec{N}$, $\vec{C_a}$, $\vec{C}$) among residues included in the coordinate set is rotation-transformed to obtain coordinates ($\vec{N'}$, $\vec{C_a'}$, $\vec{C'}$) by using one orthonormal vector set ($\vec{e_1}$, $\vec{e_2}$, $\vec{e_3}$) among sets of orthonormal vectors of five residues.

Similarly, the reference active site is also rotation-transformed by using a stored set of orthonormal vectors, and as a result, new coordinates of residue are calculated with respect to the reference active site. Referring to FIG. 5B, four new coordinate sets of four resides are created, and each new coordinate set includes new coordinates.

According to the aforementioned operations of the vector calculating unit 402 and the converting unit 404, the similarity calculating unit 410 calculates the number of overlapping residues by determining that a residue is overlapped when the transformed coordinates of the residue included in the input active site matches the transformed coordinates of the residue included in the reference active site. The similarity may be calculated according to Formula 3, but the present invention is not limited thereto.

Similarity=number of overlapping residues/number of residues of input active site [Formula 3]

When the input active site of FIG. 5A is compared with the reference active site of FIG. 5B currently being processed, since the active sites respectively have five and four residues, the active sites are compared with respect to twenty possible location matches. That is, the number of overlapping residues is calculated with respect to each of the twenty possible location matches. As a rule, the maximum calculated number of residues becomes a similarity of the reference active site currently being processed. However, to quickly perform the similarity calculation, if the calculated number of overlapping residues is greater than a critical value, the calculation of similarity with respect to the reference active site currently being processed may be ended.

Figure 7A:
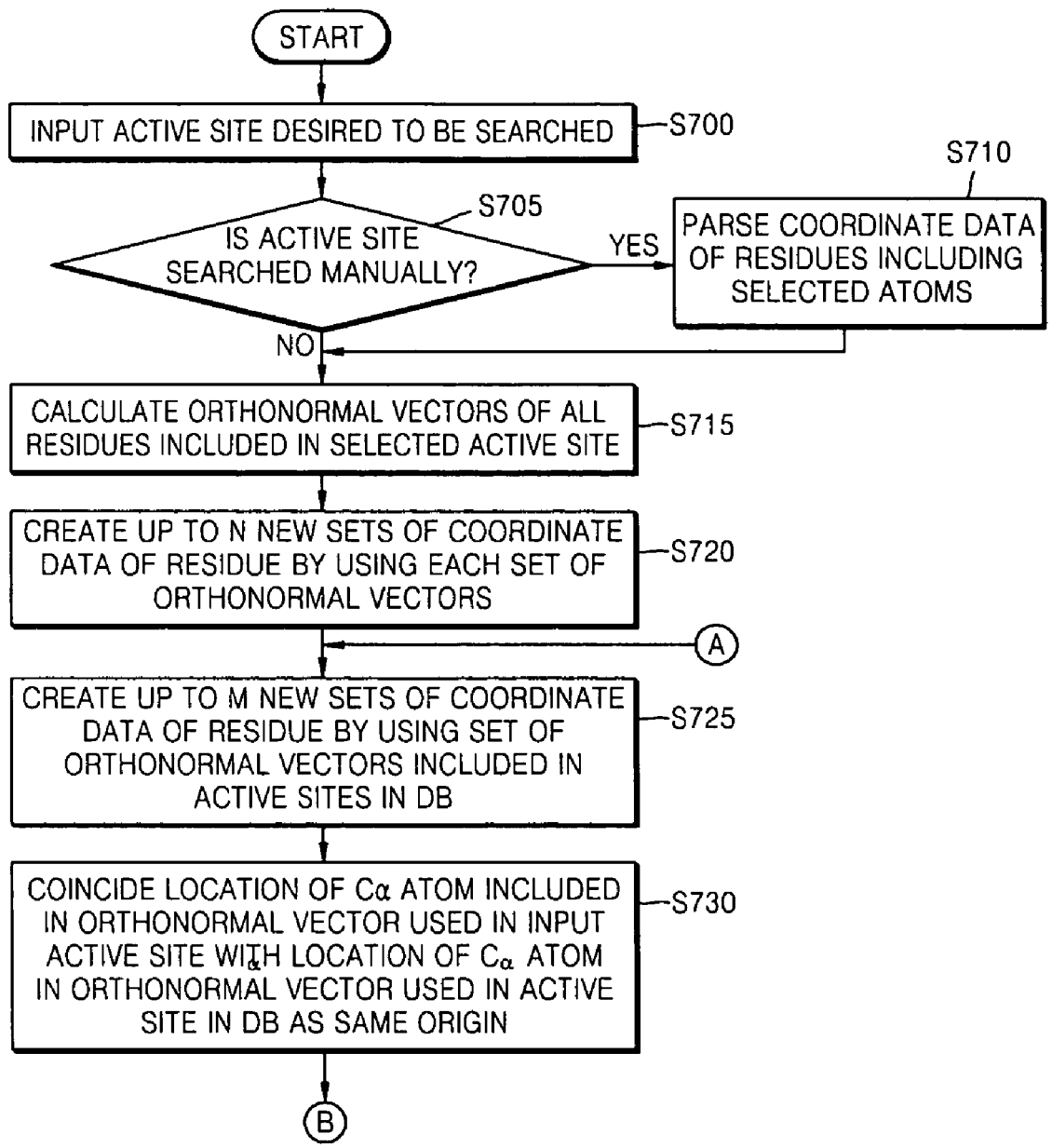
FIG. 7 is a flowchart illustrating a method of searching a protein active site according to an embodiment of the present invention.
Figure 7B:
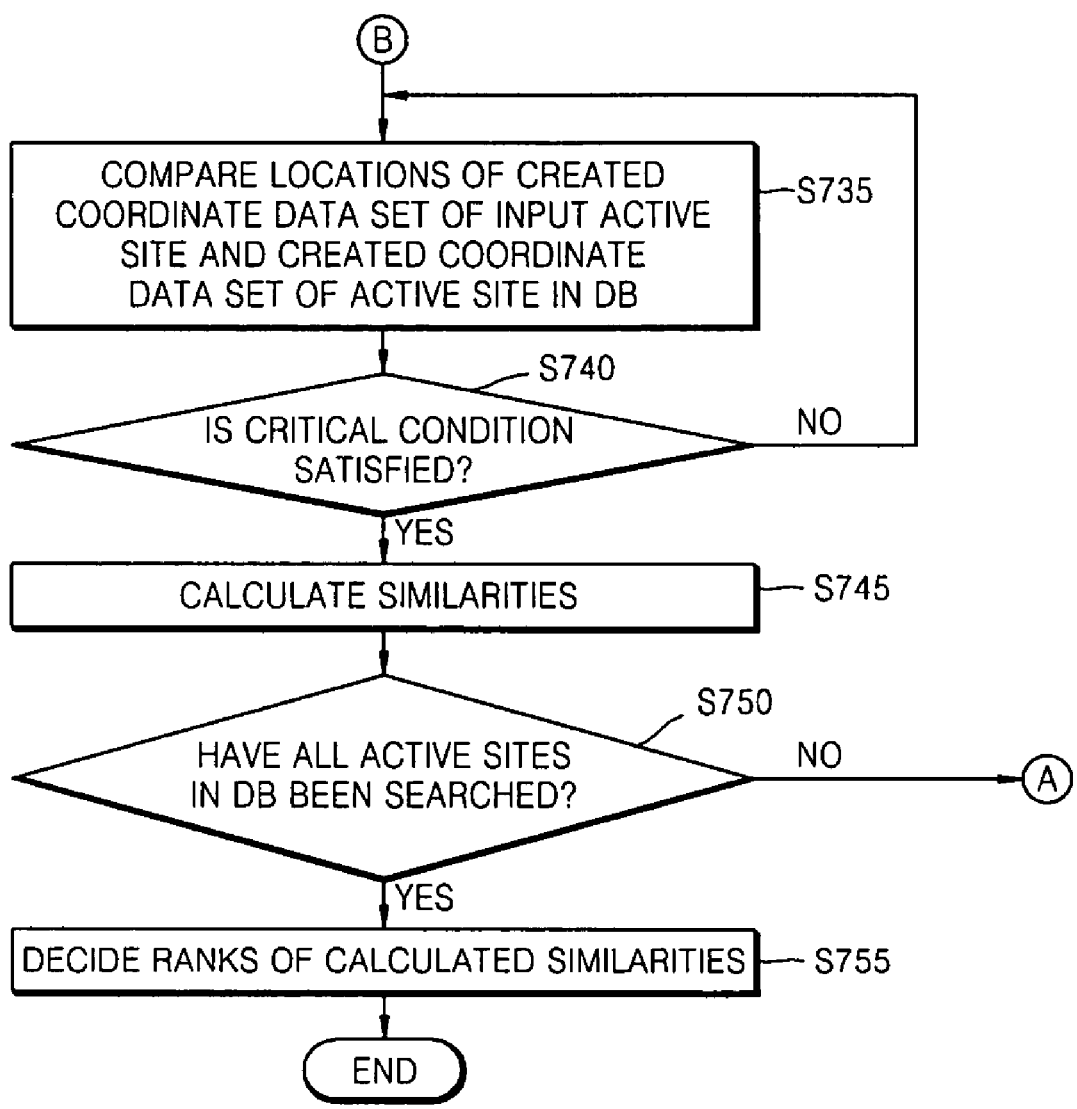

FIG. 7 is a flowchart illustrating a method of searching a protein active site according to an embodiment of the present invention. The method will be described with reference to FIGS. 1 to 4 and 7.

A PDB file is input to the PDB input unit 110 (operation S700), and then a user decides whether an active site desired to be searched is to be selected manually (operation S705) or not. If it is decided that the active site is not to be selected manually in operation S705, any one of the active sites extracted by the active site extracting unit 130 is selected. If it is decided that the active site is to be selected manually in operation S705, the user selects atoms manually while viewing a protein and atoms included in the protein that are displayed on the display unit 120, and parses location coordinates of residues including the selected atoms (operation S710). Thereafter, orthonormal vectors for all residues of the selected action site are calculated by using location coordinates of N, Cα, and C atoms as a reference frame for residue data of an active site (operation S715).

As many as n new coordinate data sets are created by the converting unit 404 (operation S720). This is because, if n residues are included in an active site, a total of n sets of orthonormal vectors are calculated, and when Formula 2 is applied to all residues in a selected coordinate data set of an active site, one coordinate set is created whenever one set of orthonormal vectors is applied to a given residue. In the same manner, with respect to active sites in the active site DB 160, a transformed coordinate vector, that is, transformed coordinate data, is obtained by using a set of orthonormal vectors in the DB table of FIG. 3 (operation S725). For example, if n residues exist in a selected active site, n coordinate data sets are transformed and obtained in operation S720. In addition, if k active sites exist in the active site DB 160, and m residues are included in a currently being processed active site, then m coordinate data sets are transformed and obtained in operation S725. In other words, coordinate data of a selected active site and coordinate data of each residue of an active site currently being processed are respectively rotation-transformed in operations S720 and S725.

After the rotation-transform is performed, coordinate data of residues of the selected active site and coordinate data of residues of the reference active site currently being processed are shift-transformed (operation S730). For example, with respect to an active site currently being processed in a selected active site and a reference active site, coordinate data may be shift-transformed after the location of the Cα atom of a residue included in an orthonormal vector used in a rotation-transform is rotation-transformed to coincide with the origin (0,0,0). Referring to FIGS. 5A and 5B, in order to perform a transformation so that the location of the Cα atom of the residue indicated by BASE in FIG. 5A coincides with the location of the Cα atom of the residue indicated by BASE in FIG. 5B, if the coordinates of the Cα atom after the residue indicated by BASE in FIG. 5A is rotation-transformed and the coordinates of the Cα atom after the residue indicated by BASE in FIG. 5B is rotation-transformed are $(x_1, y_1, z_1)$ and $(x_2, y_2, z_2)$, respectively, shift-transform matrixes $[x_1, -y_1, -z_1]^T$ and $[-x_2, -y_2, -z_2]^T$ are respectively applied to rotation-transformed coordinate data of the selected active site and rotation-transformed coordinate data of the reference active site currently being processed.

The operations S725 to S745 are performed to find a certain coordinate data set from n coordinate data sets of a selected active site and m coordinate data sets of a reference active site currently being processed, that, when used, allow residues to overlap to the maximum extent. After the shift-transform in operation S730, at least one overlapping residue is found. In this manner, locations of the n coordinate data sets of the reference active site currently being processed are compared with locations of the m coordinate data sets of the reference active site currently being processed with respect to at least one overlapping residue, and the number of overlapping residues is stored (operation S735).

The result obtained from a series of processes described above will now be explained with an example. It will be assumed that ten residues of a transformed n'th coordinate data set of an active site selected to be searched and a transformed m'th coordinate data set of a reference active site currently being processed overlap. This means that a total of ten residues overlap when the selected active site is rotation-transformed by using an n'th orthonormal vector sets of the selected active site, the reference active site currently being processed is rotation-transformed by using an m'th orthonormal vector set of the reference active site currently being processed, and then the two active sites are made to overlap by shift-transforming the transformed coordinate data sets of the reference active site with respect to the location of an nth Cα atom of the selected active site.

To improve search speed, if the number of overlapping residues satisfies a critical condition (operation S740), a similarity thereof is calculated by the similarity calculating unit 410 according to Formula 3 (operation S745). However, if the number of overlapping residues does not satisfy the critical condition (operation S740), the number of overlapping residues are stored which is obtained based on coordinate data that is rotation-and-shift transformed by using a next orthonormal vector, by returning to operation S735. Here, the critical condition may be that the number of overlapping residues is greater than ½ of the number of residues of the selected active site, but the present invention is not limited thereto.

After operation S745, an active site which has not yet been processed as described above is detected from among all active sites in the active site DB 160 (operation S750). If there is an active site which has not yet been searched, the aforementioned processes are repeated by returning to operation S725. If it is determined that all of the processes have been performed with respect to all active sites in the active site DB (operation S750), the ranks of calculated similarities are determined by the ranking unit 170.

Figure 8:
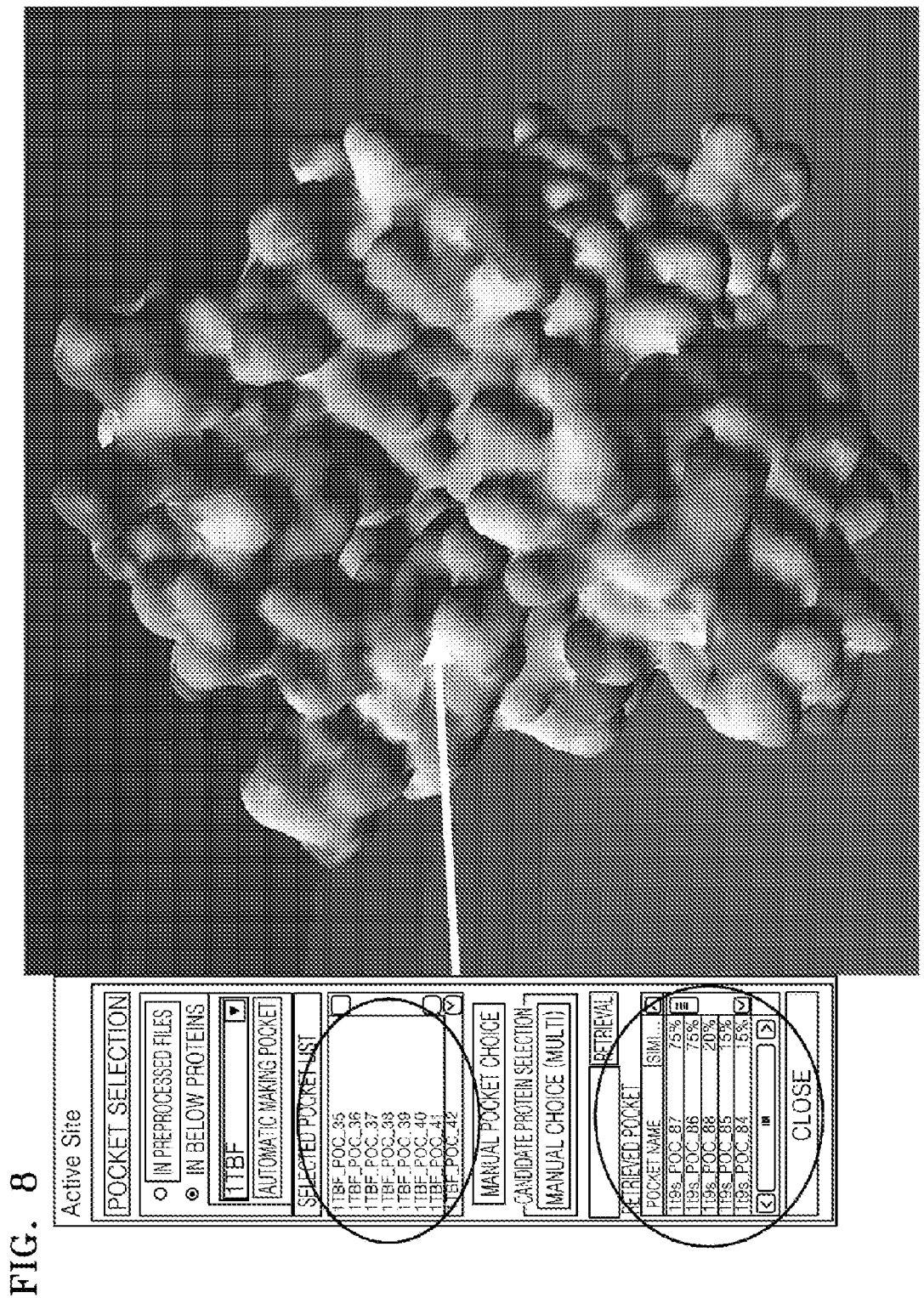
FIG. 8 illustrates a user interface used in an apparatus and method of searching a protein active site according to an embodiment of the present invention.

FIG. 8 illustrates a user interface used in an apparatus and method of searching a protein active site according to an embodiment of the present invention.

Referring to FIG. 8, a protein 1TBE is shown on a right side of a screen, and as many as 42 active sites are shown on a central left side of the screen. In the example shown in FIG. 8, a 42nd active site is selected, and a corresponding portion is a green portion indicated by an arrow on the right side of the screen, which is concaved like a pocket. A comparison search is performed when a protein 1t9s is stored in the active site DB 160. Referring to a lower left side of the screen, it can be seen that more than 87 active sites are present in the protein 1t9s, and an 87th pocket has 75% similarity.

Accordingly, the present invention can be used to obtain a correct new drug design since similar active sites can be searched with a low computational complexity. Furthermore, the present invention provides a user-friendly interface since a user can select an active site desired to be searched from an extracted active site or select the active site by using atoms displayed on a screen.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices. The computer readable recording medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. An apparatus for searching a protein active site, the apparatus comprising:
   a database which stores information on a plurality of reference active sites, wherein the information comprises coordinate data of N, Cα, and C atoms of a residue included in the reference active site, and an orthonormal vector set of the residue included in the reference active site;
   a location matching unit which matches locations of all residues included in an input active site and all residues included in the reference active site, so that at least one of the residues included in the input active site and at least one of the residues in the reference active site overlap,
   wherein the location matching unit comprises:
      a vector calculating unit which calculates an orthonormal vector set of each residue included in an input active site based on the coordinate data of the N, Cα, and C atoms of the residue in the input active site; and
      a converting unit which performs a rotation transform and a shift transform with respect to the coordinate data of N, Cα, and C atoms of the residue included in the input active site and the coordinate data of the N, Cα, and C atoms of the residue included in each of the reference active sites, by using the calculated orthonormal vector set and a stored orthonormal vector set;
      a similarity calculating unit which determines that a residue overlaps when transformed coordinate data of the N, Cα, and C atoms of the residue included in the input active site and the transformed coordinate data of the N, Cα, and C atoms of the residue included in the reference active site match and calculates 3D structural similarities based on the number of residues overlapping between the input active site and the reference active site;
      a search unit which searches the reference active sites while referring to the input active site according to the calculated 3D structural similarities; and
      a display unit which displays the searched reference active sites.

2. The apparatus of claim 1, wherein the active site database stores a name of a protein, a name of an active site included in the protein, and a name of a residue included in the active site.

3. The apparatus of claim 1, further comprising:
   an active site extracting unit which receives an input protein data bank (PDB) file including information on an active site and extracts the active site from the input PDB file; and
   an active site selecting unit which provides an active site selected from the extracted active sites by a user to the vector calculating unit as the input active site.

4. The apparatus of claim 1, further comprising:
   an active site selecting unit which receives an input protein data bank (PDB) file including information on an active site and provides an active site including an atom or residue selected from atoms or residues included in the input PDB file by a user to the vector calculating unit as the input active site.

5. The apparatus of claim 1, wherein the search unit ranks the calculated similarities.

6. A method of searching a protein active site, the method being implemented by a machine readable program code which is embodied on a computer readable medium and configured for execution by a computer, the method comprising:
   storing information on a plurality of reference active sites in a database accessible by the computer, wherein the information comprises coordinate data of N, Cα, and C atoms of a residue included in the reference active site, and an orthonormal vector set of the residue included in the reference active site;
   matching locations of all residues included in an input active site and all residues included in the reference active site, so that at least one of the residues included in the input active site and at least one of the residues in the reference active site overlap,
   wherein the matching of locations comprises:
      calculating an orthonormal vector set of each residue included in an input active site based on coordinate data of the N, Cα, and C atoms of the residue in the input active site; and
      performing a rotation transform and a shift transform with respect to the coordinate data of N, Cα, and C atoms of the residue included in the input active site and the coordinate data of the N, Cα, and C atoms of the residue included in each of the reference active sites, by using the calculated orthonormal vector set and a stored orthonormal vector set;
   determining that a residue overlaps when the transformed coordinate data of the N, Cα, and C atoms of the residue included in the input active site and transformed coordinate data of the N, Cα, and C atoms of the residue included in the reference active site match;
   calculating 3D structural similarities based on the number of residues overlapping between the input active site and the reference active site;
   searching the reference active sites while referring to the input active site according to the calculated 3D structural similarities; and
   converting the searched reference active sites into a signal for displaying the searched reference active sites using a display operatively associated with the computer.

7. The method of claim 6, wherein the storing comprises storing a name of a protein, a name of an active site included in the protein, and a name of a residue included in the active site.

8. The method of claim 6, further comprising:
   receiving an input protein data bank (PDB) file including information on an active site, and extracting the active site from the input PDB file;
   determining an active site selected from the extracted active sites by a user as the input active site.

9. The method of claim 6, further comprising:
   receiving an input protein data bank (PDB) file including information on an active site, and displaying atoms or residues included in the input PDB file; and
   determining an active site including an atom or residue selected from atoms or residues included in the input PDB file included in the input PDB file by a user as the input active site.

10. The method of claim 6, wherein the searching comprises ranking the calculated 3D structural similarities.

* * * * *